United States Patent [19]

Blanchard

[11] Patent Number: 5,144,253
[45] Date of Patent: Sep. 1, 1992

[54] METHOD AND APPARATUS FOR DETERMINING INTERACTIONS DUE TO DIRECT CURRENTS ON ADJACENT BURIED METAL STRUCTURES

[75] Inventor: Michel Blanchard, Estrees Saint Denis, France

[73] Assignee: Gaz De France, Paris, France

[21] Appl. No.: 631,319

[22] Filed: Dec. 21, 1990

[30] Foreign Application Priority Data

Dec. 27, 1989 [FR] France ................................. 89 17281

[51] Int. Cl.$^5$ .................................................. G01R 27/08
[52] U.S. Cl. ..................................... 324/715; 324/713; 324/71.1; 204/404
[58] Field of Search ....................... 324/71.1, 71.2, 713, 324/715, 724, 700; 204/153.11, 404, 196

[56] References Cited

U.S. PATENT DOCUMENTS

| | | | |
|---|---|---|---|
| 1,978,440 | 10/1934 | Shepard | 324/724 X |
| 3,355,665 | 11/1967 | Fegan, Jr. | 324/724 X |
| 4,481,474 | 11/1984 | Gerrit | 324/71.2 X |
| 4,591,792 | 5/1986 | Birchmeier et al. | 324/425 |
| 4,659,492 | 3/1972 | Marsh et al. | 324/71.2 X |
| 4,806,850 | 2/1989 | Saumade et al. | 324/71.1 |

FOREIGN PATENT DOCUMENTS 2356741  1/1978  France .

OTHER PUBLICATIONS

Seifert, R. L., "The Calculation of True Cathodic Protection Interference Drain Current from Easily Measured Data", Materials Performance, vol. 20, No. 2, pp. 19-24, Houston, 1981.

Polak, J., "The Use of Multipurpose Measuring Probes to Assess the Adequacy of Cathodic Protection of Buried Pipelines", Materials Performance, vol. 22, No. 8, pp. 12-20; Houston, 1983.

Primary Examiner—Kenneth A. Wieder
Assistant Examiner—Glenn W. Brown
Attorney, Agent, or Firm—Staas & Halsey

[57] ABSTRACT

The method of determining interactions due to direct currents on adjacent buried metal structures at least one of which is connected to a direct current generator such as a cathodic protection device, consists in placing calibrated specimen test metal pieces in the vicinity of the buried metal structures, the test pieces being made of materials that are analogous to those of the structures. The test pieces are spaced apart from each other by a distance L' equal to the distance L between the structures. Reference electrodes are placed in the immediate proximity of the specimen metal test pieces and simultaneous measurements are performed firstly of the potentials of the specimen test pieces relative to the reference electrodes, and secondly of the currents flowing through the calibrated specimen test pieces when they are electrically connected to respective ones of the structures.

19 Claims, 5 Drawing Sheets

METHOD AND APPARATUS FOR DETERMINING INTERACTIONS DUE TO DIRECT CURRENTS ON ADJACENT BURIED METAL STRUCTURES

The present invention relates to a method and to apparatus for determining the interactions due to direct currents on adjacent first and second buried metal structures, at least one of which is connected to a DC generator such as cathodic protection device.

BACKGROUND OF THE INVENTION

It is well known that the DC produced by a generator having one pole grounded propagates through the ground and may give rise to changes in the electrical state of buried works, and may degrade these works by electrolysis. Thus a buried structure connected to a DC generator producing a stable electrical current, e.g. a conventional cathodic protection device, or a DC electrified path producing stray currents, give rise ot interactions with adjacent buried metal structures, i.e. they change the potential of the metal structures as measured relative to the medium in which the structures are placed due to various current interchanges passing through the surrounding medium into the structures or from the structures into the surrounding medium. The magnitude of the current density depends on the size of the bare metal area of the structure which is in contact with the surrounding medium. The higher the current density, the greater the interaction effect of the current on a given structure.

The interactions due to direct current flows in the ground can cause a buried structure to have detrimental effects on an adjacent buried structure. Proposals have already been made to show up such interactions by monitoring the potential of each of the structures, which structures may be buried ducts, for example, by using voltmeters having high internal resistance or voltage recorders and non-polarizable electrodes placed in the ground in the vicinity of the structures. For performing the measurements, a voltmeter or a voltage recorder is connected between each of the structures and the corresponding reference electrode, and a plurality of measurements are preformed, with the DC installations being successively switched on and off. Prior methods and apparatuses for determing interactions due to direct currents are based essentially on measuring the variation of the potential of the metal in a buried structure relative to the medium in which the structure is placed. However, in practice it is difficult to interpret the measurements relating to interference between adjacent works situated in the same surrounding medium, and indeed, it is sometimes practically impossible to determine which is the interfering work and which is the work suffering interference.

Errors of interpretation are due mainly to the following three factors:

1. measurement of the duct-to-ground potential which takes account to the voltage drop in the medium caused by the flow of current;
2. the resistivity of the medium which in part determines the chemical properties of the electrolysis; and
3. the coatings of the structures which isolates them to a greater or lesser extent from the medium.

Even if the presently-favored methodology did not lend itselt to errors of interpretation, it would nevertheless lead to curative dispositions being taken but never to preventative dispositions in the event of subsequent accidental damage to the coating (or on the appearance of microcracks due to aging).

An object of the present invention is to remedy to above-mentioned drawbacks and to make it possible to monitor in reliable manner ther interactions due to direct currents on adjacent buried metal structures.

More particularly, the present invention seeks to make it possible to clarify the quality of preventative cathodic protection and to evaluate the possible interference from adjacent works, and also to verify the interference from stray currents.

Another object of the invention is to provide a method and apparatus for determining interactions accurately, reliably, easily, and enabling good-quality diagnoses to be made.

SUMMARY OF THE INVENTION

These objects are achieved, according to the invention, by an apparatus for determining the interactions due to direct currents on first and second adjacent buried metal structures, at least one of which is connected to a direct current source, such as a cathodic protection device, the apparatus comprising:

a) first and second metal calibrated specimen test pieces respectively made from materials analogous to those from which the first and second structures are made, said first and second specimen test pieces being placed in contact with the ground approximately over respective ones of said first and second buried structures in such a manner that the distance L' between the first and second specimen test pieces is substantially equal to the distance L between said first and second structures;

b) first and second reference electrodes disposed in the immediate proximity of respective ones of said first and second specimen test pieces;

c) first and second potential take-off points which are isolated relative to ground and which are provided on respective ones of said first and second metal structures;

d) a first on/off switch connected between the first isolated potential take-off point and a first current measuring device itself connected to the first specimen test piece, and a second on/off switch connected between the second isolated potential take-off point and a second current measuring device itself connected to the second specimen test piece; and e) a first single-pole changeover switch for selectively connecting one terminal of a first voltage measuring device whose other terminal is connected to the first reference electrode either to the said first potential take-off point or else to the said first specimen test piece, and a second single-pole changeover switch for selectively connecting one terminal of a second voltage measurement device whose other terminal is connected to the second reference electrode either to said second potential take-off point, or else to said second specimen test piece.

The distance d between each of the first and second buried structures and the corresponding specimen test piece is very much less than the distances between the DC sources and the buried structures.

The invention is thus based on the observation that the change is potential of a work suffering interference cannot be taken as the only criterion for determining an interaction in the context of a reference electrode which is at a greater or lesser distance or which is locally insulated by the coating on the metal to be measured. Thus, according to the present invention, account is taken simultaneously both of the potentials of the works in the ground and of the current densities flowing through calibrated specimen test pieces placed in predetermined manner relative to the buried structures.

Advantageously, the apparatus of the invention is designed to operate automatically, in which case it may further include a sample-and-hold circuit having four isolated differential paths for enabling simultaneous measurements to be performed using said first and second current measuring devices and said first and second voltage measuring devices, a first multiplexer being placed at the outputs from said sample-and-hold circuit so as to pass only one differential signal at a time, while the signals of the other paths are completely isolated, a voltage amplifier for receiving the signals from the differential paths for voltage measurements, a current amplifier for receiving the signals from the differential paths for current measurements, a second multiplexer for selecting a voltage measurement path including the voltage amplifier or a current measurement path including the current amplifier, a lowpass filter connected to the output of the second multiplexer, an analog-to-digital converter connected to the output of the lowpass filter, a microprocessor associated with a program memory and a working memory for storing data, together with a measurment sequencing and monitoring device, a real time clock, and an input-output decoder.

The sample-and-hold circuit may comprise a relay having at least eight working contacts and at least four output capacitors for storing differential voltage values applied to the four measurement paths.

The invention also provides a probe for apparatus for determining interactions due to direct currents on adjacent buried metal structures at least one of which is connected to a direct current generator such as a cathodic protection device, the probe comprising a support in the form of a plate for placing on the ground in the vicinity of a buried structure, a specimen test pieces comprising a vertical metal rod having a free bottom end in the form of a point and a body which surrounds a top portion of the rod and which is engaged in a first opening through the plate-shaped support, a reference electrode inserted at an angle through a second opening in the support, said angle lying the range about 20° to about 50° relative to the vertical, thereby presenting a bottom end engaged in the ground and emerging beneath the support plate in the vicinity of the metal rod of the specimen test pieces, and connection means for connecting the top ends of the specimen test piece and of the reference electrode to an external device for measuring voltage or current.

The metal rod may be engaged at its free top end in a metal head in the form of a spike head which includes electrical connection means. The body in the form of a sleeve and the support in the form of a plate mat be made of a plastic material such as PVC.

The invention also provides a method of determining interactions due to direct currents on first and second adjacent buried metal structures, at least one of which is connected to a direct current generator such as a cathodic protection device, the method consisting in placing first and the first and second buried metal structures, the test pieces second calibrated specimen metal test pieces in the vicinity of being made from materials analogous to those of the first and second structures, the first and second test pieces being spaced apart by a distance L' equal to the distance L between the first and second structures, in placing first and second reference electrodes in the immediate proximity of the first and second specimen metal test pieces, and in simultaneously measuring both the potentials of the first and second specimen test specimen relative to the first and second reference electrodes, and the currents flowing through the first and second calibrated specimen test pieces when the test pieces are electrically connected to the first and second structures respectively.

The potentials and the currents of the first and second specimen test pieces are measured successively under the following conditions:

a) all of the DC generators associated with the first and second structure are in operation;

b) only the DC generators associated with the first structure are in operation; and c) only the DC generators associated with the second structure, if any, are in operation.

The method may also include a step of performing instantaneous and simultaneous measurements of the potentials of the first and second buried structures and of the currents flowing through the first and second specimen test pieces which are connected without being polarized respectively to said first and second structures for a period of time not greater than about 3 seconds.

The method may also include a step of performing instantaneous and simultaneous measurements of the potentials of the first and second buried structures and of the currents flowing through the first and second specimen test pieces at least 30 minutes after uninterrupted electrical connection between the first and second specimen test pieces and respective ones of the first and second structures.

The method may also include a step of measuring the potentials of the first and second buried structures relative to the first and second reference electrodes respectively, the first and second specimen test pieces being disconnected and all DC generators associated with the first and second structures being in operation.

In a variant implementation, the method also includes a step of measuring the natural potentials of the first and second specimen test pieces relative to the first and second reference electrodes respectively while not electrically connected to the first and second structures and not less than 15 minutes after the first and second speciment test pieces have been put into place.

BRIEF DESCRIPTION OF THE DRAWINGS

An embodiment of the invention is described by way of example with reference to the accompanying drawings, in which.

DETAILED DESCRIPTION

Figure 1:
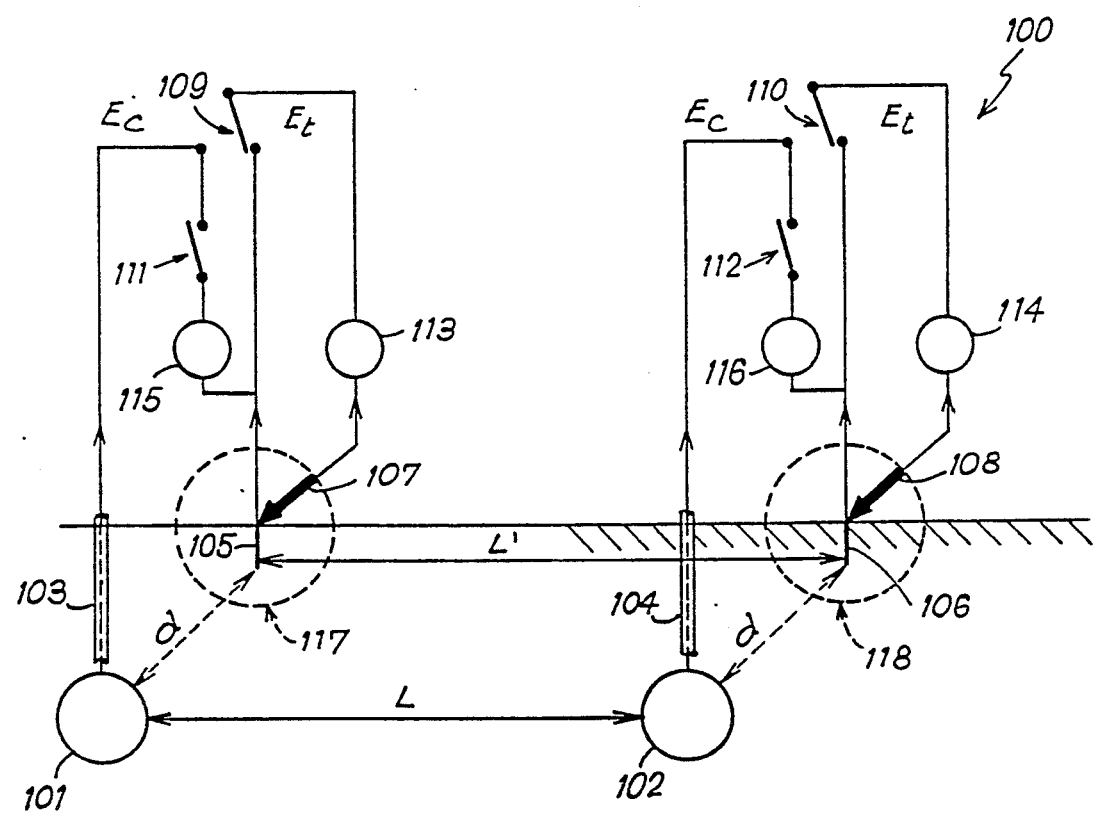
FIG. 1 is a diagrammatic vertical section through a set of apparatus for measuring interference in accordance with the invention.

FIG. 1 shows two buried metal structures 101 and 102 (hereinafter referred to variously as "structures", "ducts" or "works") such as ducts that may be used, for example, to convey water, gas, or hydrocarbons, or else that may constitute protective ducts for electrical cables. The two structures 101 and 102, are separated by a distance L, and each of them is fitted with a potential take-off point 103, 104, i.e. an electrical connection which is completely isolated from the ground and which connects the corresponding buried structure 101 or 102 to a potential measuring point situated above the ground.

In accordance with the invention, use is made of two calibrated specimen test pieces 105 and 106 that are made of the same metal or metal alloy as the buried works 101 and 102 whose interactions are to be determined (e.g. steel, cast iron, copper, lead). The specimen test pieces 105 and 106 are in the form of calibrated spikes placed over the ducts 101 and 102 and spaced apart by a distance L' which corresponds to the distance L between the ducts 101 and 102 at the location where measurements are being performed. The calibrated specimen test pieces 105 and 106 have a contact area with ground which may advantageously be about 100 cm$^2$.

The specimen test pieces 105 and 106 are thus disposed in the vicinity of the ground surface and they are very easily installed on a temporary basis when measurements are to be made in the vicinity of the potential take-off points 103 and 104 which are generally installed at the time the ducts 101 and 102 are installed. The speciment test pieces 105 and 106 need not overlie the buried structures 101 and 102 exactly, and they may be offset a little relative thereto providing the nature of the subsoil is relatively uniform. However, the distance d between each of the buried structures 101 and 102 and the corresponding specimen test piece 105, 106 should remain much less than the distances between the DC sources (such as cathodic protection devices, not shown) and the buried structures 101, 102.

Reference electrodes 107 and 108 are installed in the vicinity of the surface of the ground as close as possible to the speciment test pieces 105 and 106 so as to limit the voltage drop in the ground as much as possible while performing voltage measurements between the speciment test pieces 105 and 106 and the reference electrodes 107 and 108.

Like the speciment test pieces, the references electrodes 107 and 108 are removable and may be installed when measurements are made. Each reference electrode constitutes an un-polarizable half-cell. For example, the reference electrodes may be constituted by copper/copper sulfate electrodes (Cu/CuSO$_4$ electrodes). Advantageously, the reference electrodes 107 and 108 are small in diameter, and preferably their diameter is no greater than about 20 mm.

The assembly constituted by a calibrated specimen test piece 105 (or 106) and the corresponding reference electrode 107 (or 108) may constitute a single probe 117 (or 118) comprising a single support 2 as described in greater detail with reference to FIGS. 3 to 5. In this way, each probe 117, 118 may comprise a specimen test piece 105, 106 having a rod which is anchored substantially vertically in the ground from the surface of the ground, together with a reference electrode 107, 108 which slopes at an angle lying in the range about 20° to about 50° relative to the vertical and which has a bottom end situated in the vicinity of the ground surface in the immediate proximity of the rod anchored in the ground, with the specimen test piece and the reference electrode being held together by a common support 2.

The measurement apparatus associated with the ducts 101, 102, with the specimen test pieces 105, 106, and with the reference electrodes 107, 108 comprises on/off switches 111, 112, two single-pole changeover switches 109, 1110, two voltage measuring apparatuses 113, 114 such as millivoltmeters of high internal resistance, greater than about one megohm per volt, and two current measuring apparatuses such as milliammeters having a voltage drop of less than about 30 mV for measurement ranges lying, for example, between 50 microamps and 110 milliamps.

As can be seen in FIG. 1, the first on/off switch 111 provides a selective connection between the potential take-off point 103 on the first duct 101 and a first terminal of the milliammeter 115 whose other terminal is connected to the first speciment test piece 105. Similarly, the second on/off switch 112 provides a selective connection between the voltage take-off point 104 on the second duct 102 and a first terminal of milliammeter 116 whose other terminal is connected to the second specimen test piece 106.

The first changeover switch 109 enables one terminal of millivoltmeter 113 whose other terminal is connected to the reference electrode 107 to be selectively connected either to the potential take-off point 103 (moving switch in position Ec) or else to the specimen test piece 105 (moving switch in position Et).

Similarly, the second changeover switch 110 serves to connect one of the terminals of millivoltmeter 114 whose other terminal is connected to the reference electrode 108, selectively either to potential take-off point 104 (moving switch in position Ec) or else to the specimen test piece 106 (moving test piece in position Et).

The apparatus shown diagrammatically in FIG. 1 can be used to perform a whole series of various measurements as a function of the positions of changeover switches 109 and 110, and of on/off switches 111 and 112.

In a first step, it is possible to measure the potentials of the ducts 101 and 102 in conventional manner, with the cathodic protection or other DC sources associated with the ducts 101 and 102 being in operation. To do this, changeover switches 109 and 110 are in their positions Ec and on/off switches 111 and 112 are open.

In a second step, it is possible to measure the potentials of the specimen test pieces 105 and 106. These measurements must be performed after a stabilization period which may last about 15 minutes after the specimens have been installed. To perform these measurements, the changeover switches 109 and 110 should be in their positions Et and the on/off switches 111 and 112 should be open.

The measurements performed during the above first two steps give the initial state of the works 101 and 102 before looking for any interference.

Additional measurements serve to simulate defects in the coatings of the structures 101 and 102, with these defects being calibrated using a template (e.g. 100 cm$^2$) which has the same area as the specimen test pieces 105 and 106 that are in contact with the ground.

The additional measurements for stimulating coating defects and using the specimen test pieces 105 and 106 may be performed in two different ways.

Initally, instantaneous and simultaneous measurements are performed of the potentials of the ducts 101 and 102 and of the current flowing through the specimen test pieces 105 and 106 connected to the structures 101 and 102, but while not polarized. To do this, the changeover switches 109 and 110 are put in their positions Ec and the on/off switches 111 and 112 are closed for period of time shorter than about 3 seconds.

Thereafter, simultaneous measurements are performed of the potentials of the ducts 101 and 102 and of the currents flowing through the specimen test pieces 105 and 106 while connected permanently to the structures 101 and 102. To do this, the changeover switches 109 and 110 are kept in position Ec, and the on/off switches 111 and 112 are closed. Measurements are performed. Measurements are made, for example, at least 30 minutes after said closure.

Finally, in order to measure interaction per se, simultaneous measurements are performed of the potentials of the specimen test pieces 105 and 106 and of the currents flowing through the test pieces 105 and 106 while permanently connected to the structures 101 and 102, respectively. To do this, the changeover switches 109 and 110 are put into their positions Et, and the switches 111 and 112 are kept closed.

The polarization potentials and currents in the specimen test pieces 105 and 106 are measured successively under the following conditions:

a) all of the DC generators associated with the structures 101 and 102 are in operation;

b) only those DC generators that are associated with the first structure 101 are in operation; and c) only those DC generators that are associated with the second structure 102 (if any) are in operation.

The DC generators, e.g. cathodic protection devices, are switched off successively with respect to the structures 101 and 102 by using cyclic switches, and they are switched off for periods of less than about 3 seconds. In order to avoid the specimen test pieces 105 and 106 becoming de depolarized, the OFF periods are never greater than a value corresponding to about one-twentieth of the ON periods of the DC generator.

The various measurements performed using the apparatus of the invention may be marked up in tables such as Tables I and II at the end of the description. Table I gives the measurements of the initial state of the works 101 and 102, with the cathodic protection or other DC sources associated with these works being in operation, while Table II gives the interaction measurements per se which require the cathodic protection equipment or other DC sources associated with the works to be switched on selectively.

An analysis of the measurements marked in Table I (the inital state of the works under consideration) gives the following for each duct 101, 102, assuming that each specimen test piece has an area of 100 cm$^2$:

1) the potentials of the duct relative to the ground as measured with the conventional monitoring method;

2) the potentials spontaneously taken up by the 100 cm$^2$ specimens 105 and 106 in the medium of resistivity specific to the location of the measurements;

3) the instantaneous potentials of the duct relative to the ground while the specimens 105 and 106 are connected to the ducts 101 and 102, thereby simulating the potential drops that are created by faults having an area of 100 cm$^2$;

4) the instantaneous currents taken by 100 cm$^2$ faults prior to polarization (for estimating the protective current density in each of the works);

5) the potentials of each duct relative to the ground while the specimens 105 and 106 are permanently connected; and 6) the magnitudes of the protective currents through the specimens 105 and 106 after polarization.

This series of measurements is used as a reference for improving interpretation of the interaction measurements per se.

The results marked in Table II (interaction measurements) may give rise to three situations:

1) with the cathodic protection of the works 101 and 102 in operation, if the direction of current flow through one of the specimens 105 or 106 is observed to reverse, then current is escaping and thus metal is being lost from one of the specimens 105 or 106, and this means that dangerous, unfavorable interference is taking place;

2) with the cathodic protection of the works 101 and 102 being switched off in succession, either:

a) the direction of current flow through the specimen 105 or 106 of the work 101 or 102 whose protection is switched off is observed to reverse, which means that dangerous unfavorable interference is taking place; or b) the current flowing one of t he specimens 105 or 106 is reduced, which means that unfavorable interference is taking place. More thorough analysis of the potentials and the current densities needs to be performed. The action decided on will take account of criteria relating to voltage and to current density (e.g. 1000 mV and 50 mA/m$^2$).

If one of the works 101 and 102 is not fitted with cathodic protection, it will not suffer from interference if the cathodic protection of the other work does not give rise to exit current from the specimens.

3) During successive switching off of the cathodic protectionto the works 101 and 102, if one of the works is "favorably" interferred with, i.e. if there is an increase in the protective current flowing through the corresponding specimen 105 or 106, then additional measurements should be performed to determine the locations where current leaves the work being interferred with.

The graphs of FIGS. 6 to 9 show various different possible interactions between a structure 50 which constitutes an "interferring" work, i.e. a work from which interference is being exerted, and a structure 60 which constitutes an "interferred with" work, i.e. a work which is subjected to interference. Each of the structures 50 and 60 is represented by a vertical line, and vectors 51 to 53 and 61 to 63 represent a current entering or leaving the structure depending on the direction of the arrow relative to the corresponding vertical line, and the magnitude of the current is represented by the length of each vector symbol.

In each of FIGS. 6 to 9, the vectors 51 to 53 and 61 to 63 are determined by implementing the method of the invention, i.e. by simultaneously measuring potentials and polarization currents in the specimen test pieces 105 and 106 associated with the structures 101 and 102 as symbolized by the lines 50 and 60.

The vectors 51 and 61 represent the currents applied to (or taken from) the works 101 and 102 respectively when all of the DC generates associated with the structures 101 and 102 are in operation.

The vectors 52 and 62 represent currents entering or leaving the works 101 and 102 respectively when only the DC generator(s) associated with the first structure 101 is/are in operation.

The vectors 53 and 63 represent the currents entering and leaving the works 101 and 102 respectively when only the DC generator(s) associated with the second structure 102 is/are in operation.

Figure 6:
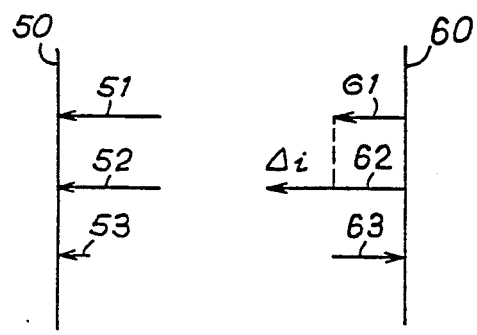
FIGS. 6 to 9 are vector diagrams showing the interference due to direct current between two structures under four different sets of interactions.

FIG. 6 corresponds to dangerous unfavorable interference exerted by the structure represented by line 50 on the structure represented by line 60. It can be seen that regardless of whether the DC sources associated with the structure 60 are in operation or not in operation, the vectors 61 and 62 show current leaving it. The vector 63 shows current entering it when the DC source associated with the structure 50 is not in operation.

Figure 7:
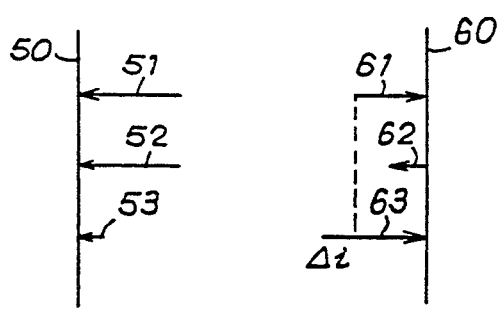

FIG. 7 corresponds to damaging unfavorable interference exerted by the structure 50 on the structure 60. When the DC source associated with the structure 60 is not in operation, then the current vector 62 relating to the structure 60 shows that current is leaving the structure. In contrast, the vector 63 shows that current enters it when the DC source associated with the structure 50 is not in operation. The vector 61 shows current entering the structure corresponding to the algebraic sum of the vectors 62 and 63, as occurs when the DC sources for both structures 50 and 60 are in operation.

Figure 8:
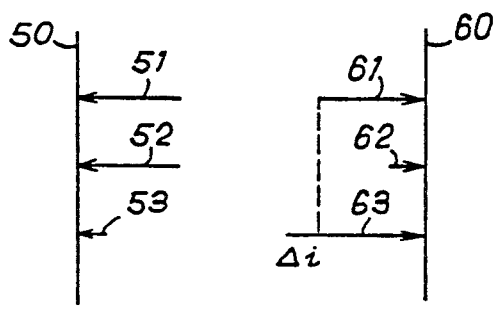

FIG. 8 corresponds to non-damaging unfavorable interference being exerted by the structure 50 on the structure 60. Providing the normal criteria relating to potentials and current densities are satisfied, it can be seen that under all circumstances, the currents 61, 62, and 63 are in the form of currents entering the structure 60 even if the magnitudes of these currents are at a minimum when the DC source associated with the structure 60 is not in operation (vector 62) and if the magnitude of the current entering is at a maximum when the DC source associated with the structure 50 is not in operation (vector 63).

Figure 9:
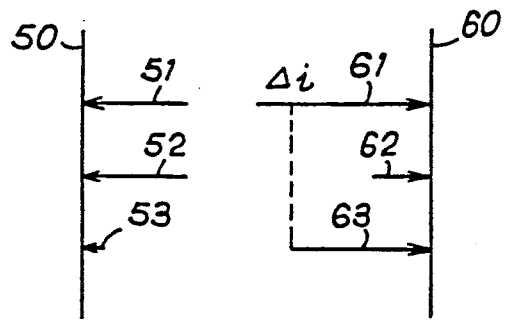

FIG. 9 corresponds to favorable interference being exerted by the structure 50 on the structure 60. As in FIG. 8, all of the currents 61, 62, 63 are currents that enter the structure 60, however in FIG. 9 it is the vector 61 which corresponds to all of the DC sources associated with both structures 50 and 60 of the operation that is the vector corresponding to the current of maximum magnitude. The minimum magnitude vector is the vector 62 corresponding to the case where the current source associated with the structure 60 is not in response. In the case shown in FIG. 9, it is necessary to lock for zones where current is leaving the structure 60.

One example of electronic circuits suitable for implementing automatic apparatus for measuring interference in accordance with the invention is now described with reference to FIG. 2.

Figure 2:
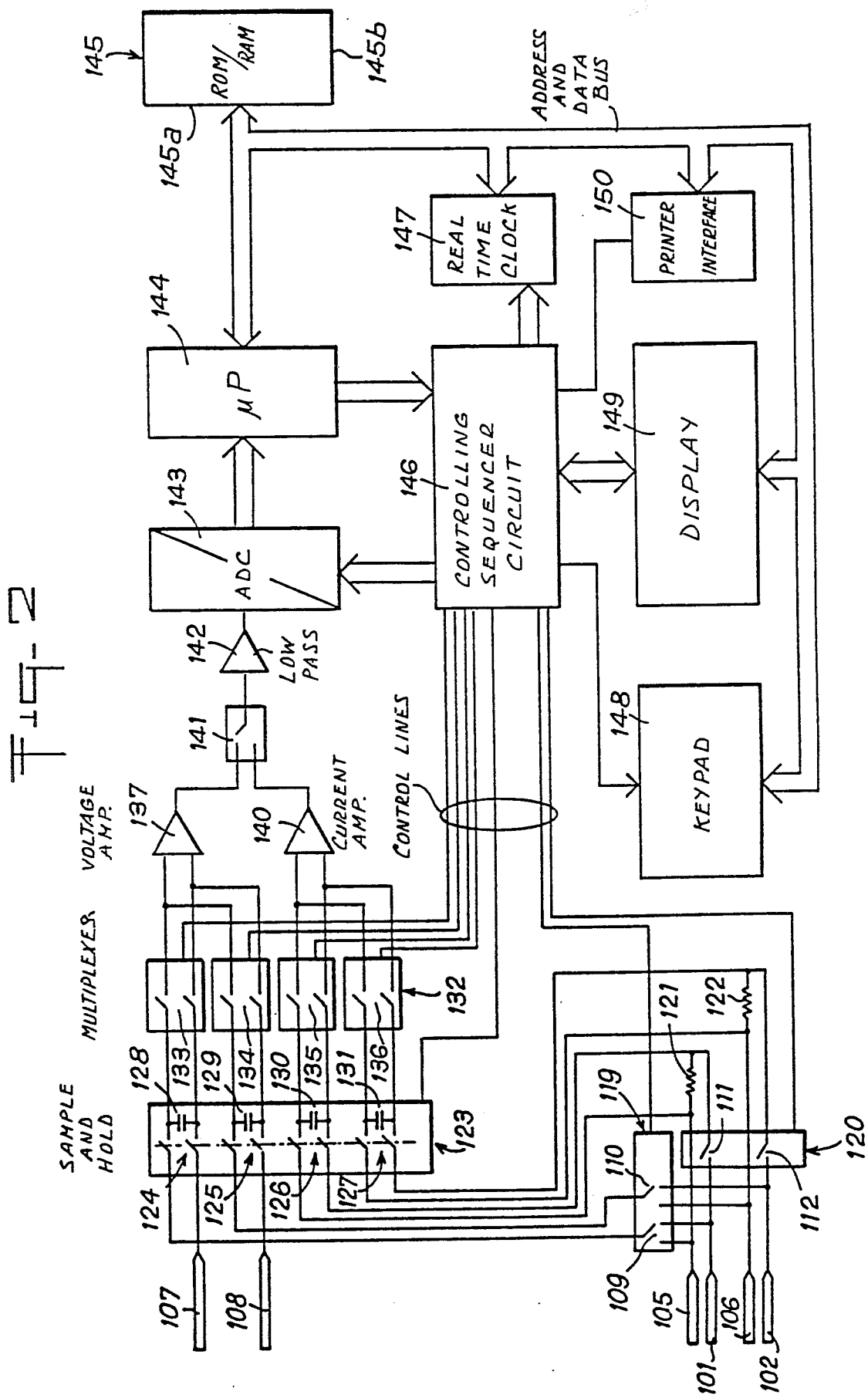
FIG. 2 is a block diagram showing the various component parts of the electronic circuits incorporated in automated interference measuring apparatus of the invention.

In FIG. 2, the metal structures 101 and 102, the specimen tast pieces 105 and 106, and the reference electrodes 107 and 108 are all represented symbolically to show their various electrical connections with the circuits of the measurement apparatus via relays 119 and 120 constituting the changeover switches 109 and 110, and the on/off switches 111 and 112. Resistors 121 and 122 are connected in series with the contacts of the switches 111 and 112 respectively, and constitute shunts for measuring the magnitudes of the polarization currents flowing between the specimen 105 and the structure 101, and between the specimen 106 and the structure 102.

A sample-and-hold circuit 123 has four isolated differential channels 124 to 127 enabling simultaneous measurements to be performed on the four measurement paths constituted by the current measurement paths 126 and 127 (taking signals from the terminals of the shunts 121 and 122) and by the voltage measurement paths 124 and 125 (taking differential voltage signals forrm across the moving contacts of the changeover switches 109 and 110 respectively, which switches are capable of being selectively connected to respective structures 101 and 102 or to respective specimen test pieces 105 and 106, and to respective reference electrodes 107 and 108). The sample-and-hold circuit 123 is constituted by a relay having eight working contacts and provided with output capacitors 128 to 131 in each channel 124 to 127 for storing the measured values.

The signals from the sample-and-hold circuit 123 are directed to a multiplexer 132 which comprises four pairs of electronic switches 133 to 136 corresponding to the four measurement paths and controlled selectively from a control circuit 146 so as to pas only one differential signal at a time while completely isolating the other signals.

Depending on the types of measurement to be performed (voltage measurements for measurement paths 124, 128, 133 and 125, 129, 134, and current measurements for measurement paths 126, 130, 135 and 127, 131, 136) the signals are directed either to a voltage amplifier 137 or to a current amplifier 140.

A second multiplexer 141 then selects a voltage path or a current path and directs the signals to a lowpass filter 142 for eliminating electrical interference. The output from the filter 142 is connected to an analog-to-digital converter 143 which transmits the measured value to a microprocessor 144. The microprocessor 144 is connected by an address bus and a data bus to memories 145 including a program memory 145a and a working memory 145b for storing data. The microprocessor 144 controls the order in which connections are established using a real time clock 147 to time the various operations, and a monitoring and sequencing circuit 146 for the various measurements, and further including an input/output decoder and a user interference connected to a controlling keypad 148 for entering parameters and enabling an operator to specify which measurement stages are to be performed. A display 149 (e.g. a liquid crystal display having four lines each of twenty-four characters) is connected to the circuit 146 to display the results of measurments and to specify which operation is taking place. An interface 150 may also be connected to the control circuit 146 to enable all of the results to be reproduced on a printer.

For simultaneous measurement of four values (two voltage values and two current values) enabling the method of the present invention to be implemented, the automatic apparatus of FIG. 2 uses the control circuit 146 to send control pulses to the relays 119 and 120 and a control pulse to the ACQ input of the sample-and-hold circuit 123 in order to cause it to take samples simultaneously on all paths. The values of the measurements are stored temporarily by charging the capacitors 128 to 131. The control circuit 146 may then select the paths 133 to 136 one after another via the SEL inputs of the multiplexer 132, thereby providing, after amplification, filtering, and analog-to-digital conversion, digital values representing the first and second voltages and the first and second currents. It may be observed that although the apparatus of FIG. 2 makes use of only one analog-to-digital converter 143, the measurements it performs are nevertheless genuinely simultaneous.

An example of a probe which is particularly suited to implementing the method of the present invention and which performs the functions of the probes referenced 117 and 118 in FIG. 1 is described below in greater detail and with reference to FIGS. 3 to 5.

Figure 3:
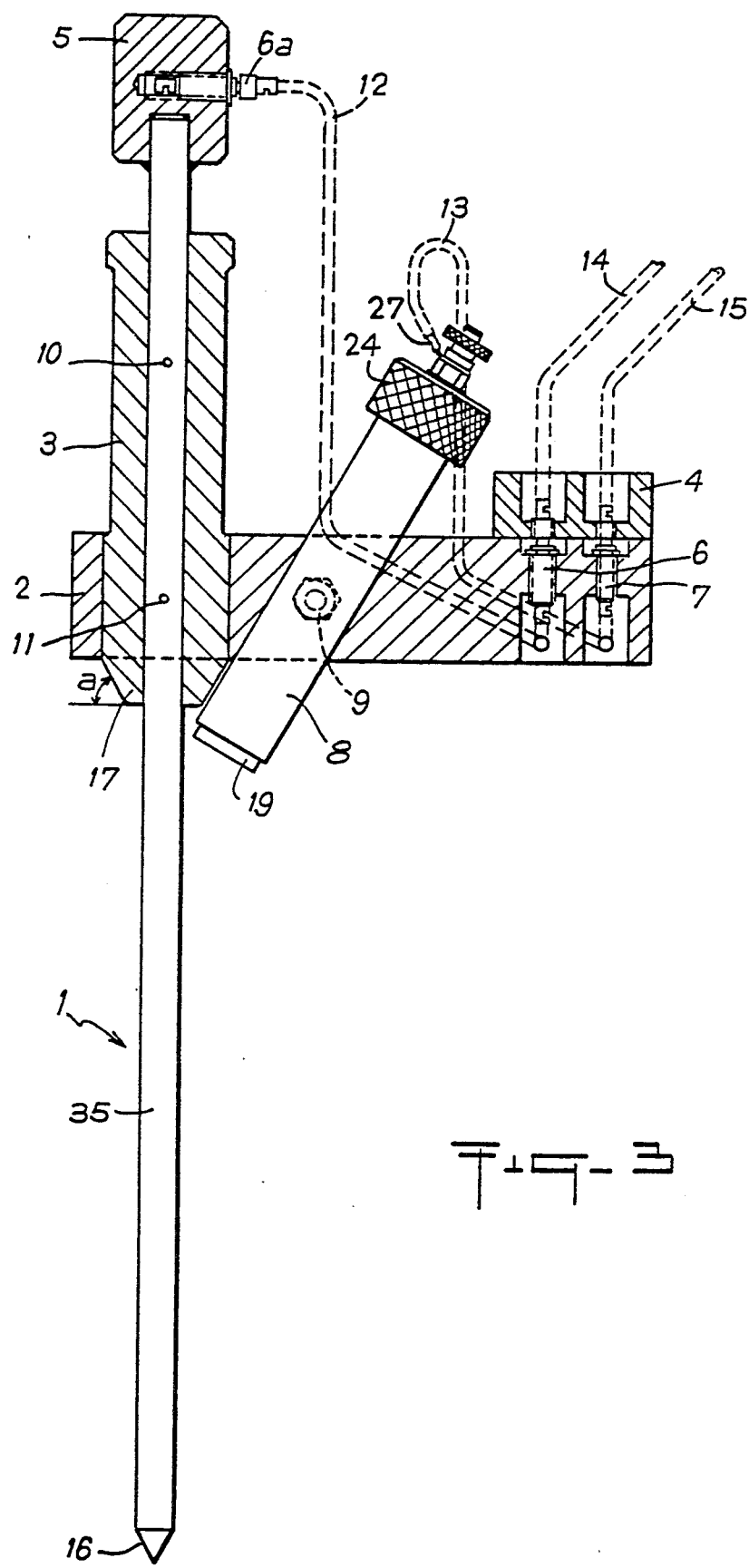
FIG. 3 is a vertical section through a probe comprising a calibrated specimen test piece and a reference electrode and suitable for being used in the interference measuring apparatus of FIGS. 1 and 2.
Figure 4:
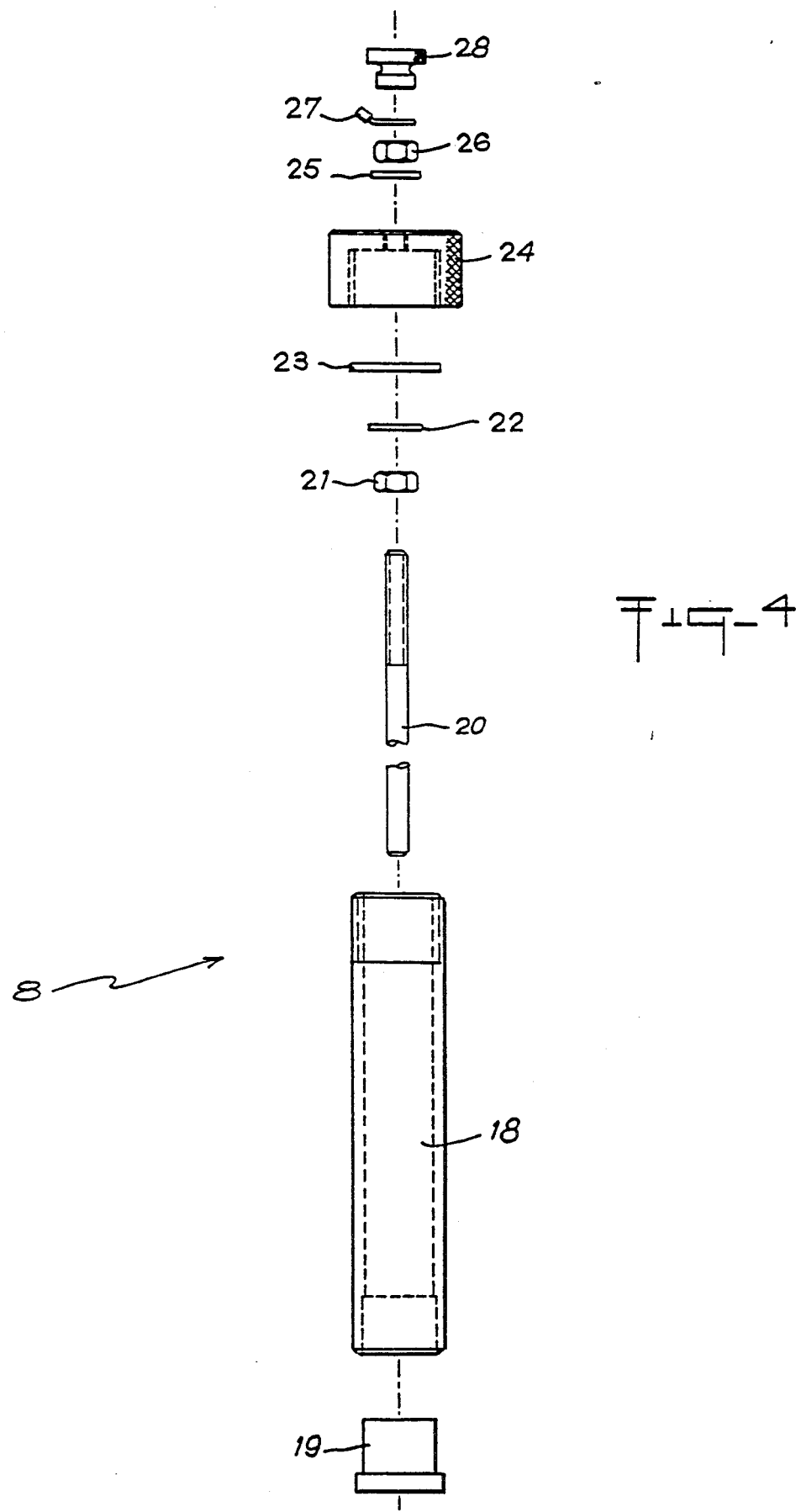
FIG. 4 is an exploded elevation view of the reference electrode used in the probe of FIG. 3.
Figure 5:
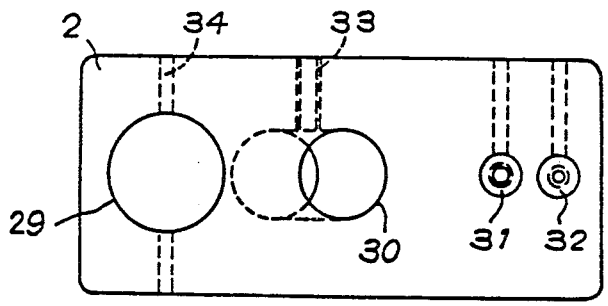
FIG. 5 is a plan view of a common support for the probe of FIG. 3.

The probe shown in FIGS. 3 to 5 comprises a common insulating support 2 both for a specimen test piece 1 and for a reference electrode 8 that are intended to be installed on the surface of the ground substantially over a buried metal structure that may give rise to interactions with an adjacent buried metal structure.

The support 2 is in the form of a plate (see FIG. 5) which may be made of a plastic material such as PVC. The support plate 2 is intended to have its bottom face resting on the ground. The plate 2 has a first through hole 29 in which the insulating body 3 constituting the handle of the specimen test piece 1 is engaged. An orifice 30 whose axis slopes relative to the vertical to converge towards the axis of the specimen test piece 1 beneath the plate 2 is provided to receive the reference electrode 8. Two other holes 31 and 32 are formed through the plate 2 for receiving connection sockets 6 and 7 which are connected via connection wires 12 and 13 respectively to a connection pin 6a for connection with the head 5 of the specimen test piece 1 and with a connection tab 27 for connection to the reference electrode 8 (FIG. 3). A connector 4 made of plastic material such as PVC and provided with two pins of different sections is provided to engage the sockets 6 and 7 and provide electrical connections via wires 14 and 15 from the specimen test piece 1 and the reference electrode 8 to the measurement circuits as constituted by components 109, 111, 113, 115 or 110, 112, 114, 116 in FIG. 1 or components 119 to 150 in FIG. 2.

The specimen test piece 1 in FIG. 3 is in the form of a spike having a metal head 5 engaged on a central metal rod 35 and terminated by a point 16 at its bottom end. The portion of the central rod 35 which emerges from the body 3 for holding it in the support 2 is polished and has a calibrated surface area, which may be about 100 cm², for example. The body 3 and the rod 35 are held together by pins 10 and 11. The bottom portion 17 of the body 3 projects beneath the plate 2 over a short distance in the form of a truncated cone which engages in the surface of the ground and enable the bottom end 19 of the reference electrode 8 (e.g. constituted by a wooden plug) to come into the immediate vicinity of the buried rod 35 in the uppermost portions of the subsoil. The electrode 8 comprises a body 18, e.g. a PVC body, held in the support 2 by means of a screw 9, and a central metal bar 20 which is made of copper if the electrode is of the Cu/CuSO₄ type. FIG. 4 shows the top plug 24 of the electrode 8 provided with a knurled outside face and a thread on its inside face. Reference 21 designates an internal nut for holding the central bar of the electrode, reference 22 designates a washer, and reference 23 designates a sealing washer. The top end of the bar 20 which emerges from the top plug 24 itself co-operates with a washer 25, a first nut 26, an electrical connection tab 27, and a second top nut 28 which has a knurled outside surface.

TABLE I

Measurements of the initial state of the works (cathodic protection for works A and B in operation)

| MEASUREMENT | WORK A | WORK B |
|---|---|---|
| (1) Duct/ground voltage (mV) Specimens not connected | | |
| (2) Specimen/ground voltage (duct not connected) (mV) | | |
| (3) Duct/ground voltage (mV) specimens connected <3 s Magnitude of protection current (mA) in non-polarized specimens | | |
| (4) Ground/duct voltage with specimens connected (mV) (polarization time >30 m) Specimen currents (mA) after polarization (time >30 minutes) | | |

TABLE II

Interaction measurements using the method of the invention

| PROTECTION SITUATION | WORK A | | | | WORK B | | | |
|---|---|---|---|---|---|---|---|---|
| | Et (mV) | δEt (mV) | It (mA) | δIt (mA) | Et (mV) | δEt (mV) | It (mA) | δIt (mA) |
| a) Work A on Work B on | | xxx | | xxx | | xxx | | xxx |
| | | xxx | | xxx | | xxx | | xxx |
| b) Work A on Work B off | | | | | | | | |
| c) Work A off Work B on | | | | | | | | |

Note:
Et = polarized specimen voltage permanently connected to the duct.
It = polarization current flowing through specimen.

I claim:

1. Apparatus for determining the interactions due to direct currents on first and second adjacent buried metal structures, at least one of which is connected to a direct current source, such as a cathodic protection device, wherein the apparatus comprises:
   a) first and second metal calibrated specimen test pieces respectively made from materials analogous to those from which the first and second structures are made, said first and second specimen test pieces being placed in contact with the ground approximately over respective ones of said first and second buried structures in such a manner that the distance L' between the first and second specimen test pieces is substantially equal to the distance L between said first and second structures;
   b) first and second reference electrodes disposed in the immediate proximity of respective ones of said first and second specimen test pieces;
   c) first and second potential take-off points which are isolated relative to ground and which are provided on respective ones of said first and second metal structures;

d) a first on/off switch connected between the first isolated potential take-off point and a first current measuring device itself connected to the first specimen test piece, and a second on/off switch connected between the second isolated potential take-off point and a second current measuring device itself connected to the second specimen test piece; and e) a first single-pole changeover switch for selectively connecting one terminal of a first voltage measuring device whose other terminal is connected to the first reference electrode either to the said first potential take-off point or else to the said first specimen test piece, and a second single-pole changeover switch for selectively connecting one terminal of a second voltage measuring device whose other terminal is connected to the second reference electrode either to said second potential take-off point, or else to said second specimen test piece.

2. Apparatus according to claim 1, wherein the distance d between each of the first and second buried structures and the corresponding specimen test piece is substantially less than the distance between the direct current source and the corresponding one of the buried structures.

3. Apparatus according to claim 1, wherein the first and second reference electrodes are of the $Cu/CuSO_4$ type and the diameter thereof is not greater than 20 mm.

4. Apparatus according to claim 1, wherein the area in contact with the ground of each of the first and second calibrated specimen test pieces is about 100 $cm^2$.

5. Apparatus according to claim 1, wherein the first and second current measurement devices include first and second shunts, respectively.

6. Apparatus according to claim 1, further including a sample-and-hold circuit having four isolated differential paths for enabling simultaneous measurements to be performed using said first and second current measuring devices and said first and second voltage measuring devices, a first multiplexer being placed at the outputs from said sample-and-hold circuit so as to pass only one differential signal at a time, while the signals of the other paths are completely isolated, a voltage amplifier for receiving the signals from the differential paths for voltage measurements, a current amplifier for receiving the signals from the differential paths for current measurements, a second multiplexer for selecting a voltage measurement path including the voltage amplifier or a current measurement path including the current amplifier, a lowpass filter connected to the output of the second multiplexer, an analog-to-digital converter connected to the output of the lowpass filter, a microprocessor associated with a program memory and a working memory for storing data, together with a measurement sequencing and monitoring device, a real time clock, and an input/output decoder.

7. Apparatus according to claim 6, wherein the sample-and-hold circuit comprises a relay having at least eight working contacts and at least four output capacitors for storing differential voltage values applied to the four measurement paths.

8. Apparatus according to claim 1, wherein the first calibrated specimen test piece and the first reference electrode are mounted on a common support.

9. Apparatus according to claim 1, wherein the second calibrated specimen test piece and the second reference electrode are mounted on a common support.

10. Apparatus according to claim 1, wherein each of the first and second specimen test pieces comprises a rod anchored substantially vertically in the ground and extending downwardly from the surface of the ground, and wherein each of the first and second reference electrodes is inclined at an angle of 20° to 50° relative to the vertical, having a bottom end situated in the vicinity of the surface of the ground in the immediate proximity of said rod anchored in the ground.

11. A method of determining interactions due to direct currents on first and second adjacent buried metal structures, at least one of which is connected to a direct current generator such as a cathodic protection device, wherein the method comprises the steps of placing first and second calibrated specimen metal test pieces in the vicinity of the first and second buried metal structures, the test pieces being made from materials analogous to those of the first and second structures, the first and second test pieces being spaced apart by a distance L' equal to the distance L between the first and second structures, placing first and second reference electrodes in the immediate proximity of the first and second specimen metal test pieces, and simultaneously measuring both the potentials of the first and second specimen test pieces relative to the first and second reference electrodes, and the currents flowing through the first and second calibrated specimen test pieces when the test pieces are electrically connected to the first and second structures respectively.

12. A method according to claim 11, wherein both the first and second structures are connected respectively to first and second direct current generators and wherein the potentials and the currents of the first and second specimen test pieces are measured successively under the following conditions:

a) the first and second direct current generators associated with the first and second structures are in operation;

b) only the first direct current generator associated with the first structure is in operation; and c) only the second direct current generator associated with the second structure is in operation.

13. A method according to claim 12, wherein while performing said potential and current measurements on the first and second specimen test pieces measurements are performed requiring DC generators to be taken out of operation for periods of time shorter than about 3 seconds.

14. A method according to claim 11, further including a step of performing instantaneous and simultaneous measurements of the potentials of the first and second buried structures and of the currents flowing through the first and second specimen test pieces which are connected without being polarized respectively to said first and second structures for a period of time not greater than 3 seconds.

15. A method according to claim 11, further including a step of performing instantaneous and simultaneous measurements of the potentials of the first and second buried structures and of the currents flowing through the first and second specimen test pieces at least 30 minutes after uninterrupted electrical connection between the first and second specimen test pieces and respective ones of the first and second structures.

16. A method according to claim 11, further including a step of measuring the potentials of the first and second buried structures relative to the first and second reference electrodes respectively, the first and second specimen test pieces being disconnected and all DC generators associated with the first and second structures being in operation.

17. A method according to claim 11, further including a step of measuring the natural potentials of the first and second specimen test pieces relative to the first and second reference electrodes respectively while not electrically connected to the first and second structures and not less than 15 minutes after the first and second specimen test pieces have been put into place.

18. A probe apparatus for determining interactions due to direct currents on adjacent buried metal structures at least one of which is connected to a direct current generator such as a cathodic protection device, wherein the probe comprises a support in the form of a plate for placing on the ground in the vicinity of a buried structure, a specimen test piece comprising a vertical metal rod having a free bottom end in the form of a point and a body which surrounds a top portion of the rod and which is engaged in a first opening through the plate-shaped support, a reference electrode inserted at an angle through a second opening in the support, said angle lying in the range of 20° to 50° relative to the vertical thereby presenting a bottom end engaged in the ground and emerging beneath the support plate in the vicinity of the metal rod of the specimen test piece, and connection means for connecting the top ends of the specimen test piece and of the reference electrode to an external device for measuring voltage or current.

19. A probe according to claim 18, wherein the metal rod is engaged at its free top end in a metal head in the form of a spike head which includes electrical connection means, and the body is in the form of a sleeve and the support in the form of a plate are made of a plastic material such as PVC.

* * * * *

UNITED STATES PATENT AND TRADEMARK OFFICE
CERTIFICATE OF CORRECTION

PATENT NO. : 5,144,253  
DATED : September 1, 1992  
INVENTOR(S) : Michel Blanchard PAGE 1 of 2

It is certified that error appears in the above-indentified patent and that said Letters Patent is hereby corrected as shown below:

TITLE PAGE [56] References Cited, line 6, "4,659,492" should be --3,649,492--.

Column 1, line 20" ot" should be --to--.

Column 3, line 61, after "first and" insert --second calibrated specimen metal test pieces in the vicinity of the--;
line 62, after "pieces" insert --being made from materials analogous to those of the first and second--;
lines 62-64, delete "calibrated specimen ... and second".

Column 5, line 2 and 3, delete "(hereinafter .... "works");
line 8, after "102," insert --(hereinafter referred to variously as "structures", "ducts" or "works")--;
line 45, "speciment" should be --specimen--.

UNITED STATES PATENT AND TRADEMARK OFFICE
CERTIFICATE OF CORRECTION

PATENT NO. : 5,144,253
DATED : September 1, 1992
INVENTOR(S) : Michel Blanchard

It is certified that error appears in the above-indentified patent and that said Letters Patent is hereby corrected as shown below:

Column 6, line 10, "1110" should be --110--.

Column 7, line 11, after "for" insert --a--;
lines 18 and 19, delete "Measurements are performed.".

Column 8, line 29, delete "t he" and substitute --the--;
line 42, delete "protectionto" and substitute --protection to---.

Column 9, lines 51 and 52, "response" should be --operation--;
line 53, "lock" should be --look--.

Column 10, line 10, "form" should be --from--.

Signed and Sealed this

Twenty-sixth Day of October, 1993

Attest:

BRUCE LEHMAN

*Attesting Officer*    *Commissioner of Patents and Trademarks*